United States Patent [19]

Ramey

[11] Patent Number: 5,753,474
[45] Date of Patent: May 19, 1998

[54] CONTINUOUS TWO STAGE, DUAL PATH ANAEROBIC FERMENTATION OF BUTANOL AND OTHER ORGANIC SOLVENTS USING TWO DIFFERENT STRAINS OF BACTERIA

[75] Inventor: David Edward Ramey, Reynoldsburg, Ohio

[73] Assignee: Environmental Energy, Inc., Columbus, Ohio

[21] Appl. No.: 771,065

[22] Filed: Dec. 20, 1996

Related U.S. Application Data

[60] Provisional application No. 60/009,215, Dec. 26, 1995.
[51] Int. Cl.$^6$ .................. C12P 7/40; C12P 7/56; C12P 7/54; C12P 7/14
[52] U.S. Cl. .................. 435/136; 435/42; 435/139; 435/140; 435/141; 435/150; 435/157; 435/160; 435/162; 435/813; 435/842
[58] Field of Search .................. 435/42, 160, 141, 435/140, 136, 139, 150, 162, 157, 842, 813

[56] References Cited

U.S. PATENT DOCUMENTS

| | | |
|---|---|---|
| 1,315,585 | 9/1919 | Weizmann . |
| 4,326,032 | 4/1982 | Grove . |
| 4,539,293 | 9/1985 | Bergstrom et al. . |
| 5,063,156 | 11/1991 | Glassner et al. . |
| 5,132,217 | 7/1992 | Gabelman . |
| 5,192,673 | 3/1993 | Jain et al. . |

OTHER PUBLICATIONS

A.S. Afschar; H. Biebl, K. Schaller, and K. Schügerl, "Production of acetone and butanol by *Clostridium acetobutylicum* in continuous culture with cell recycle", *Applied Microbiology and Biotechnology* (1985) 22:394–398.

A.S. Afschar; K. Schaller; and K. Schügerl, Continuous production of acetone and butanol with shear–activated *Clostridium acetobutylicum*, *Applied Microbiology and Biotechnology* (1985) 23:315–321.

Hubert Bahl; Wolfram Andersch; and Gerhard Gottschalk, "Continuous Production of Acetone and Butanol by *Clostridium acetobutylicum* in a Two–Stage Phosphate Limited Chemostat", *European Journal of Applied Microbiology and Biotechnology* (1982) 15:201–205.

David T. Jones and David R. Woods, "Solvent Production", Biotechnology Handbooks #3, P.N. Minton, 1989, D.J. Clarke, Plenjum Press, New York, N.Y. 10013, p. 135.

P.G. Krouwel, Continuous Production of n–Butanol And Isopropanol By Immobilized, Growing *Clostridium butylicum* Cells, Biotechnol. Lett. 2:253–258 (1980).

Michael R. Ladisch, "Fermentation–derived butanol and scenarious for its uses in energy–related applications", *Enzyme Microb. Technol.*, 1991, Mar., 13:280–283.

John A. Marlatt and Rathin Datta, "Acetone–Butanol Fermentation Process Development and Economic Evaluation", *Biotechnology Progress* (vol. 2, No. 1): pp. 23–28 (1986).

D. Michael–Savin, R. Marchal, and J.P. Vandescastelle, 1990, "Butyric fermentation: metabolic behavior and production performance of *Clostridium tyrobutyricum* in a continuous culture with cell recycle", *Applied Microbiology and Biotechnology*, 34:172–177.

Frédéric Monot, Jean–Marc Engasser, and Henri Petitdemange, 1984, Influence of pH and undissociated butyric acid on the production of acetone and butanol in batch cultures of *Clostridium acetobutylicum*, *Applied Microbiology and Biotechnology*, 19:422–426.

Samuel Cate Prescott, Sc.D. and Cecil Gordon Dunn, Ph.D., 1949, "Industrial Microbiology", McGraw–Hill, New York, pp. 312–351.

David E. Ramey, 1995, "Emerging Technologies In Butanol Production", Environmental Energy, Inc., in house monograph. pp. 1–29.

Juergen Wiegel, Seung–Uk, KUK, and Gert W. Kohring, 1989, "*Clostridium thermobutyricum* sp. nov., a Moderate Thermophile Isolated from a Cellulolytic Culture, That Produces Butyrate as the Major Product", *International Journal of Systematic Bacteriology*, 39 (2): 199–204.

*Primary Examiner*—Herbert J. Lilling
*Attorney, Agent, or Firm*—Frank H. Foster; Kremblas, Foster, Millard & Pollick

[57] ABSTRACT

The instant invention describes a process for the manufacture of butanol and like volatile organic compounds by fermenting carbohydrates, mainly polysaccharide, with micro-organisms which convert carbohydrates into mainly butyric acid and other acids. The acids are subsequently transferred to the solventogenesis production stage using a different strain of bacteria which continuously produces butanol and like volatile organic compounds, via a multistage fermentation process that is stable, high yielding (weight product per unit weight carbohydrates) and productive (faster throughput). By employing one microbe (the first) in the major pathway to produce the acid of choice specifically and faster, and provide for another microbe (the second) with the unique property to convert the acid to a solvent, carbohydrates are not wasted on ancillary product. The unique advantage of the second microbe is that it has the capability of converting acids into solvents (solventogenesis). For example *Clostridium acetobutylicum* passes though two morphologies, first acid producing (acidogenesis), yielding acetic, butyric, and lactic acids from the carbohydrate source. Then *C. acetobutylicum* shifts its physiology into a solventogenesis phase for the latter part of its life cycle, converting the acids it produced through acidogenesis into acetone, butanol, ethanol and isopropanol. The instant invention increases the yield by decreasing the production of ancillary acids and alcohols. It increases the volumetric productivity since the first bacteria produces butyric or a like acid faster and in a better yield than the second bacteria.

12 Claims, 1 Drawing Sheet

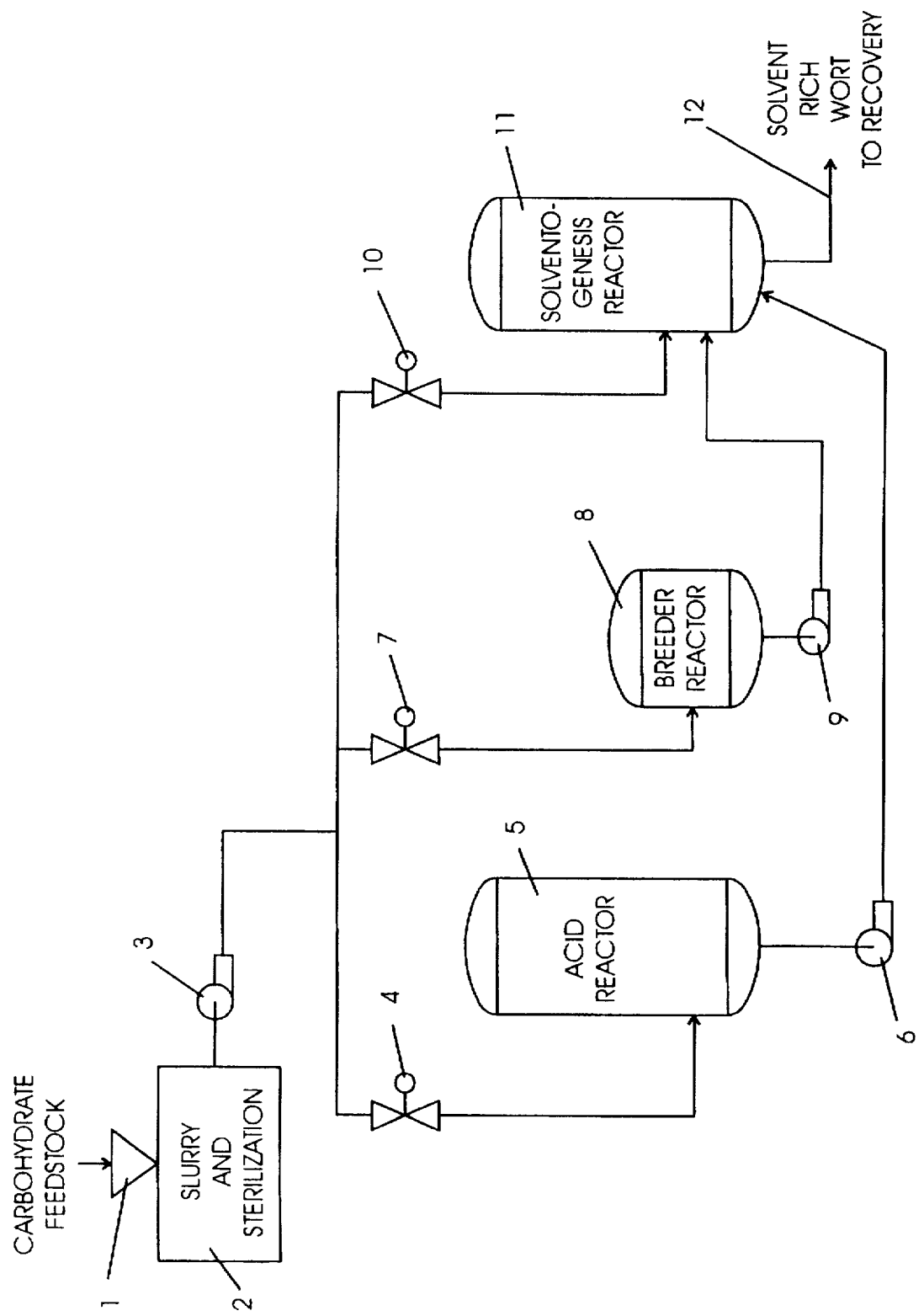

5,753,474

CONTINUOUS TWO STAGE, DUAL PATH ANAEROBIC FERMENTATION OF BUTANOL AND OTHER ORGANIC SOLVENTS USING TWO DIFFERENT STRAINS OF BACTERIA

This application claims the benefits of U.S. Provisional Application No. 60/009,215 filed Dec. 26, 1995.

FIELD OF THE INVENTION

The present invention relates to a process for the manufacture of butanol or similar volatile organic compounds by the anaerobic fermentation of carbohydrates by multiple micro-organisms.

DESCRIPTION OF PRIOR ART

Fermentation of carbohydrates to acetone, butanol, and ethanol (ABE) is well known. These solvents were commercially produced by fermentation process since 1919 and the Weizmann patent is most noted. Clostridium acetobutylicum has been the organism of choice for conducting this fermentation. In the 1950s with the advent of new petrochemical processes and low cost crude oil, the fermentation based processes became economically unattractive and most of the commercial installations were shut down. In recent years, the increased cost of petrochemical feedstocks stimulated enactment of U.S. legislation to produce strategic chemicals, fuels, and energy from domestic renewable resources. This has caused a renaissance of this historical fermentation process, the development of improved bacterial strains (Marlatt 1986) and processes for commercialization (Ramey 1995).

The old fermentation processes were batch processes with low productivity and low solvent concentration. Corn mash is generally used as a carbohydrate source. Based on old batch process data and design, an economical evaluation of the fermentation process with corn carbohydrates was found to be unattractive (Ladisch, 1991).

Yields of butanol from carbohydrates (weight product per unit weight carbohydrates) by current technology is on the order of 20–25% (Prescott 1949) and 22.7% (Marlatt 1986). Productivity rates (weight of product (gram) with respect to volume of fermentation system (liter) per unit time (hour): g/l/h) according to Krouwel (1980) are 1.0–2.5 g/l/h, while Afschar (1985) reports 1.3–3.0 g/l/h at different conditions of cell mass concentrations and dilution rates with the highest being 4.5 g/l/h. Mutant strains have been developed that withstand greater concentration of volatile organic compounds, but even a 60% improvement only increases productivity rates from 1.2 to 2.0 g/l/h. Strains which produce preponderantly butyric acid with cell recycling have a volumetric productivity of greater than 9.5 g/l/h (Michel-Savin, 1990). Gabelman (1992) reported a continuous process for the production of butyric acid for the flavor industry using Clostridium tyrobutyricium and mono- or di-saccharides as feedstock.

Multiple strains of bacteria have been used but only in synergy within the same slurry. Groves (1982) uses a consortium of bacteria to help digest cellulose for the production of acetone, butanol, ethanol (ABE) as organic fuel production. Bergstrom (1985) used as examples in a single stage system a coculture of microorganism of Clostridium genus concurrently in the same reaction vessel, one favoring the production of butyric acid from a monosaccharide which is then converted to butanol by the second genus and he claimed an increase of more than 20% in the yield over the use of one microorganism. Many continuous multistage reactor systems have been used for ABE fermentation (Bahl 1982) and (Afschar 1986) but still yields and volumetric productivity are relatively low.

The instant invention increases the yield and volumetric productivity for fermentation derived butanol or other volatile organic compounds from carbohydrate sources mainly polysaccharides. The invention deals with polysaccharides, cellulose, hemicellulose, starches and sugars and not just simple sugars.

An object of the present invention is to provide a continuous process for the production of butanol which significantly improves its yield.

A further object of the invention is to provide a continuous process with high volumetric productivity (measured in weight of product per volume of reactor per unit time—generally grams per liter per hour—g/l/h), thereby reducing the throughput time per unit weight of butanol produced.

BRIEF SUMMARY OF THE INVENTION

The invention is a continuous process for preparing solvents by digesting carbohydrates in the anaerobic fermentation of a carbohydrate slurry. The major portion of the carbohydrate slurry and a first acid-producing bacteria are fed into an acid reactor. The continuous fermentation of the carbohydrate in the acid reactor as a result of the activity of the first bacteria forms a solution which includes a short chain organic acid, such as butyric acid. A minor portion of the carbohydrate slurry and a second solvent producing bacteria are fed into a breeder reactor to breed the second bacteria in an acidogenesis phase. The acid solution is extracted from the acid reactor and transferred to a solventogenesis reactor. The acidogenesis bacteria from the breeder reactor are transferred to the solventogenesis reactor. The anaerobic fermentation of the extracted acid as a result of the activity of the second bacteria forms a solution including a short chain alcohol, such as butanol. The alcohol solution is extracted from the solventogenesis reactor at a rate sufficient to maintain the solventogenesis fermentation. The alcohol is separated from the solution.

BRIEF DESCRIPTION OF THE DRAWING

The FIGURE is a diagram illustration of the method of the present invention.

In describing the preferred embodiment of the invention which is illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose.

DETAILED DESCRIPTION

The objective of the instant invention is for the manufacture of butanol and like volatile organic compounds by anaerobically fermenting carbohydrates with multiple strains of micro-organisms. Suitable carbohydrate feedstocks include corn and other such products which have sugar, starch and cellulose components. One strain is used in a major digestive pathway and converts carbohydrates into mainly butyric acid and other acids in an acid reactor. These acids are transferred to a solventogenesis stage reactor which uses at least one other strain of bacteria in a solventogenesis phase, generated in a minor digestive pathway, to continuously produce butanol and like volatile organic compounds, via a multistage fermentation process.

The present invention may use in the major pathway strains of anaerobic bacteria such as *Clostridium tyrobutyricum, C. thermobutyricum, C. butyricum, C. cadaveros, C. cellobioparum, C. cochlearium, C. felsineum, C. pasteurianum, C. roseum, C. rubrum, C. sporogenes,* and other microbes which produce a preponderance of butyric acid and other acids (Jones 1989). These bacteria are used for the major consumption of incoming carbohydrates and producing mainly butyric acid and other acids. The acids are then fed to a different strain of anaerobic bacteria in its solventogenesis phase physiology, for the conversion of acids to solvents. Such bacteria as: *Clostridium acetobutylicum, C. beijerinkii, C. aurantibutyricum,* and *C. tetanomorphum,* or similar bacteria, through solventogenesis digest carbohydrates, butyric acid and other acids, converting them to solvents such as butanol, acetone, ethanol, isopropanol and other volatile organics.

According to one aspect of the present invention there is provided a process for the manufacture of mainly butanol and like volatile organic compounds. The process includes the steps of fermenting in a reactor a major portion of incoming carbohydrates with micro-organisms that convert the carbohydrates into a preponderance of mainly butyric acid and other acids. The acids are continuously transferred from this primary fermentation pathway to the solventogenesis reactor containing solventogenesis phase bacteria. This pathway converts acids and minor amounts of incoming carbohydrates to butanol and like volatile organic compounds. In a minor pathway the biomass is fed into a smaller reactor with the second bacteria with the conditions adjusted to favor acidogensis then it is transferred to the larger breeder reactor where it shifts into a solventogenesis phase. Thereby this process utilizes bio-masses containing carbohydrates, mainly polysaccharides more efficiently.

According to a further aspect of the present invention there is provided for in the process a major pathway to digest carbohydrates, in which the bacteria of choice has a higher volumetric productivity for butyric acid than the minor digestive pathway has for its solventogenesis phase. By increasing the volume of the solventogenesis reactor, in order to handle the increased production of incoming acids, an increase is realized in overall volumetric productivity of butanol through the system.

The instant invention is a much more efficient process compared to previous methods of single bacterial strains, such as *C. acetobutylicum*, with an increase in yield of 39% to 52%, for converting incoming carbohydrates to butanol and other like volatile organic compounds and also an increase in volumetric productivity of more than 78%.

An increase in yield is obtained with the instant invention by using the carbon source from carbohydrates more effectively. The invention uses multiple strains of Clostridium bacteria in two continuous and simultaneous pathways through the acidogenesis and solventogenesis phases.

Hubert Bahl (1982) and Ramey (1995), have observed that in a two stage continuous fermentation process the solventogenesis phase, of *C. acetobutylicum,* has the advantage of converting glucose and butyric acid into butanol. The embodiment of this patent breeds solventogenesis stage *C. acetobutylicum,* or a like bacteria in a minor pathway and uses the solventogenesis stage bacteria to produce butanol from butyric acid generated by a major digestive pathway. The major portion of incoming carbohydrates are digested by *C. thermobutyricum, C. tyrobutyricum,* or a like acid producing bacteria, to produce large amounts of mainly butyric acids and other acids (such as acetic, and lactic).

These acids are then converted into butanol and less of other solvents (such as acetone, ethanol, and isopropanol) by the solventogenesis stage of *C. acetobutylicum,* or a like bacteria.

This process increases the yield of butanol obtained from a given amount of carbohydrates compared to other systems by creating a preponderance of butyric acid which is then converted to mainly butanol and only minor amounts of all the other carbon based by-products such as lactic acid, acetic acid, acetone, ethanol and isopropanol as are produced with most single strains of bacteria such as *C. acetobutylicum.*

Clostridium acetobutylicum

In all strains of Clostridium large amounts of carbon dioxide are produced, generally 40–50%. Prescott (1949) states that from 1,000 lbs. of corn, which contained 650 lbs. of starch, when *C. acetobutylicum* is used for digesting the 650 pounds of starch: 163 lbs. of n-butanol (25%), 70 lbs. of acetone (11%), 407 lbs. of carbon dioxide (63%), 11 lbs. of hydrogen (1.7%), and 12 lbs. of residual acid (1.8%) were obtained. (Table 1.)

$$\frac{163 \text{ lbs. butanol}}{650 \text{ lbs. starch}} = 25.1\% \text{ Butanol}$$

$$\frac{163 \text{ lbs. butanol}}{1000 \text{ lbs. corn}} = 16.3\% \text{ Butanol}$$

Prescott (1949) further states that from 3 lbs. of starch, with conversion via *C. acetobutylicum,* 1 lb of mixed solvents results. Therefore it can be assumed according to the normal ratio of 6:3:1 (butanol, acetone and ethanol), that 0.6 lb. butanol (20%) 0.3 lb. acetone (10%), and 0.1 lb. of ethanol (0.3%) may be obtained.

$$\frac{0.6 \text{ lb. butanol}}{3 \text{ lb. starch}} = 20\% \text{ Butanol}$$

TABLE 1

*Clostridium acetobutylicum*
(Prescott, 1949)
Optimal Temperature 37–42° C. and a pH range of 5.0–7.0

| Substance | Formula | GMW | Production Weight lbs. | % Yield |
|---|---|---|---|---|
| Corn | | | 1000 | |
| Starch | $(C_6H_{10}O_5)_n$ | 150k–600k | 650 | 100% |
| Non-starch | | | 350 | |
| Carbon Dioxide | $CO_2$ | 44 | 407 | 62.6% |
| Hydrogen | H | 1 | 11 | 1.6% |
| Residual acids | | | 12 | 1.8% |
| Acetone | $C_3H_6O$ | 58 | 70 | 10.8% |
| Butanol | $C_4H_{10}O$ | 74 | 163 | 25.1% |

Clostridium thermobutyricum

*Clostridium thermobutyricum* exhibits the following properties.

In the production of a preponderance of butyric acid (*C. thermobutyricum* for example Wiegel, 1989) glucose is converted to 44% carbon dioxide, 13% acids (acetic and lactic) and 41.6% butyric acid (Table 2.). The latter has the potential of being converted into 34.9% butanol (assuming 100% conversion/yield).

TABLE 2

*Clostridium thermobutyricum*
[Wiegel 1989]
Optimal Temperature 55° C., pH range of 6.8–7.1

| Substance | Formula | GMW | moles | W/R GMW | % | % Acid |
|---|---|---|---|---|---|---|
| Glucose | $C_6H_{12}O_6$ | 180 | 1.00 | 180 | 100% | |
| Carbon Dioxide | $CO_2$ | 44 | 1.80 | 79.2 | 44.0% | |
| Butyric acid | $C_4H_9O$ | 88 | 0.85 | 74.8 | 41.6% | 76% |
| Lactic acid | $C_3H_6O_3$ | 90 | 0.20 | 18.0 | 10.0% | 18% |
| Acetic acid | $C_2H_4O_2$ | 60 | 0.10 | 6.0 | 3.3% | 6% |
| Hydrogen | H | 1 | 1.90 | 1.9 | 1.1% | |
| Butanol* | $C_4H_{10}O$ | 74 | 0.71 | 62.9 | 34.9% | |

*potential for butyric acid conversion (100%) to Butanol on a gram molecular weight basis.

Propensity for butanol:

$$\frac{41.6\% \text{ butyric acid} \times 74 \text{ } GMW \text{ butanol}}{88 \text{ } GMW \text{ butyric acid}} = 34.9\% \text{ yield}$$

Therefore: the incoming carbohydrates could yield 34.9% butanol.

This is a much more efficient process compared to the use of *C. acetobutylicum* with an increased yield of butanol from starch by 39%:

$$\frac{(34.9\% \text{ C. thermobutyricum} - 25.1\% \text{ C. acetobutylicum})}{25.1\% \text{ C. acetobutylicum}} = 39\% \text{ increase}$$

*Clostridium tyrobutyricum*

Similar properties exist for *C. tyrobutyricum* as for *C. thermobutyricum*. Michel-Savin (1990), reports that a continuous culture of 65 grams per liter (g/l) glucose using *C. tyrobutyruicum* produces a preponderance of butyrate of 29.7 g/l (45.9%), which has the potential of being converted to 24.9 g/l (38%) butanol.

Propensity for butanol:

$$\frac{(29.7 \text{ g/l butyric acid} \times 74 \text{ } GMW \text{ butanol})}{88 \text{ } GMW \text{ butyric acid}} = 24.9 \text{ g/l butanol}$$

equivalent to $$\frac{(45.7\% \text{ butyric acid} \times 74 \text{ } GMW \text{ butanol})}{88 \text{ } GMW \text{ butyric acid}} = 38.4\% \text{ yield}$$

When comparing the possible yield from *C. tyrobutyricum* to the standard yield from the *C. acetobutylicum* strain an increase of 53% can be realized.

$$\frac{(38.4\% \text{ C. thermobutyricum} - 25.1\% \text{ C. acetobutylicum})}{25.1\% \text{ C. acetobutylicum}} =$$

52.9% increase

In the *C. tyrobutyricum* reaction the potential for conversion of butyric acid to butanol is 38% of the incoming carbohydrates. This is compared to 25% when using only ABE pathway with *C. acetobutylicum*. This is a 53% increase in the effective use of carbohydrates to produce butanol, because the carbon source is not used to produce multiple by-products such as acetone, ethanol, isopropanol and associated acids (lactic and acetic).

An increase in the volumetric productivity of 78% can be realized in the major pathway since *C. tyrobutyricum* exhibits a volumetric productivity potential for butyric acid of greater than 9.5 g/l/hr butyrate (Michel-Savin 1990), which is then converted into butanol (8 g/l/h) by the instant invention, compared to volumetric productivity using *C. acetobutylicum* in continuous culture with cell recycling the highest obtained of 4.5 g/l/hr (Afschar, 1985).

$$\frac{(8.0 \text{ g/l/h C. tyrobutyricum} - 4.5 \text{ g/l/h C. acetobutylicum})}{4.5 \text{ g/l/h C. acetobutylicum}} =$$

78% increase

This 78% increase in volumetric productivity was calculated from the highest value of 4.5 g/l/h found in the literature (Afschar 1985) for *C. acetobutylicum* while the normal volumetric productivity is on the order of 1.0 to 2.5 g/l/h (Marrlott, 1986 and Krouwel 1980).

Further the increase in volumetric productivity most probably more than 78%, since the system is a multi-stage and dual pathway, where butanol is derived from the major pathway as well as from the minor pathway.

Therefore, to summarize, increasing the solventogenesis reactor volume by 4 times, for ABE solventogenesis phase of *C. acetobutylicum* or like bacteria, the input from the highly productive butyric acid producing bacteria stream can be handled and a continuous stream of butanol can be produced at the rate far greater than current volumetric productivity of *C. acetobutylicum* strains and mutants alone.

This invention involves the breeding of *C. acetobutylicum* into its solventogenesis physiology. Generating solventogenesis phase bacteria, through cell recycling, in order to consume the volumetric input from a primary strain of micro-organisms such as, *C. thermobutyricum*, *C. tyrobutyricum* or the like bacteria, which produce butyric acid at an increased productivity rate.

Therefore, the instant process becomes more energy efficient in producing butanol or the like volatile organic compounds because of better and faster usage of the incoming carbohydrates, by increasing the yield and the volumetric productivity, thereby reducing capital and overall manufacturing costs.

References to FIG. 1 are as follows:

TABLE 3

| | |
|---|---|
| 1. Material Preparation | 7. Proportional Feed Valve |
| 2. Slurry & Sterilization System | 8. Breeder Reactor |
| 3. Slurry Pump | 9. Acid Pump |
| 4. Proportional Feed Valve | 10. Proportional Feed Valve |
| 5. Acid Reactor | 11. Solventogenesis Reactor |
| 6. Acid Pump | 12. Product Outlet |

Referring now to FIG. 1, Carbohydrate containing material, enters the carbohydrates preparation system 1 to be milled and/or micronized. Milling reduces the size of incoming carbohydrates making it easier to decompose by the selected bacteria. Sterilization 2 kills background bacteria allowing bacteria of choice to flourish in selected reactors 5, 8, & 11.

Carbohydrates are mixed with water to form a slurry and then steriziled as is common to all fermentation systems. The slurry is proportionally added to selected reactors through Slurry Pump 3 and the appropriate Proportional Feed Valves 4, 7 & 10. The major portion of the sterile slurry from Slurry Pump 3 is transferred through Proportional Feed Valve 4 to the Acid Reactor 5. Acid Reactor 5 receives the sterile carbohydrate mash and converts it to butyric acid by the first bacteria. The butyric acid, after sterilization or filtration to remove the first bacteria, is then fed as it is produced by Acid Pump (6) to the Solventogenesis Reactor (11), for conversion to butanol. Only butyric and other acids are transferred to the solventogensis reactor from the major digestive pathway reactor. Since cell recycling is carried out in all reactors, a technique known to those skilled in the art, the liquid containing acids transferred to the solventogensis reactor for conversion to mainly butanol is free of the major digestive pathway microbes which would compete for food with the second microbe if allowed to be transferred to the solventogensis reactor. Other means would be to sterilize any liquids transferred from the major digestive pathway to the solventogensis reactor via ohmic, pulsed electric or steam according to the definition of biological sterilization.

Sterile carbohydrates slurry is simultaneously fed as needed along a minor pathway from the Pump 3 through Proportional Feed Valve 7 to Breeder Reactor 8 to breed the second bacteria of choice. These bacteria are transferred by Acid Pump 9 to the Solventogenesis Reactor 11. This procedure replenishes and assures active solventogenesis phase bacteria which digest carbohydrates and acids to produce solvents.

The main sterile carbohydrates slurry is further proportionally fed through Proportional Feed Valve 10 to the Solventogenesis Reactor 11 to help supply energy to the solventogenesis phase bacteria. Wort containing solvents is transferred to the Solvent Recovery System through Product Pump 12. In the solventogenesis reactor, solvent levels are kept at lower levels than those that inherently inhibit the action of the microbes of choice. For example: C. acetobutylicum becomes sluggish at 1.0% total solvents and generally sporilate or die at 1.5% total solvent concentration. Therefore, the solvents are continuously recovered keeping the solvent levels below 1.0%.

Typically, the Acid Reactor 5 is kept at a temperature of about 53° C. and a pH range between 6.8 to 7.1 for C. thermobutyricum (Wiegel 1989). Other parameters optimized for other butyric acid producing bacteria would be adjusted appropriately. Breeder Reactor 8 is kept at about 36° C. and a pH of 5.5±0.25 and the Solventogenesis Reactor 11 is kept at about 37° C. and a pH of about 4.3–4.4 in accordance with the characteristics of C. acetobutylicum (Afschar 1985). However, other butanol or volatile organic compounds producing bacteria might have other parameters, such as thermophiles and the Reactors 5, 8 & 11 working temperature and pH would be adjusted in accordance with the selected bacteria. Butanol and other volatile organic compounds are removed continuously from the Solventogenesis Reactor 11 by activate charcoal, membranes or per vaporation or other technologies known to the art in order to maintain vibrant growth and conversion of acids into solvents. The Solvent depleted wort is returned to the reactor or discarded in order to maintain reactor fluid levels.

The advantage of separating the activity of two distinct microbes is to allow for different growing characteristics such as temperature and pH in order to take advantage of the capability of one microbe acting with a faster digestive rate, for example, one producing acids at grams per liter per hour and the other at only 1 gram per liter per hour. The invention uses two or more microbes which act at different rates, pH, and temperatures. If more than two microbes are used, then additional reactors would be used when different growth characteristics are expressed. The use of a co-culture or a consortium of microbes restricts the use of two or more microbes which then must function at the same temperature and pH. To take advantage of any thermophile bacteria, the temperature is generally higher for its functioning than non-thermophiles, such as C. acetobutylicium. In a coculture or consortium, both strains would not survive due to the difference in operating temperatures. The method of the invention selectively promotes the production of butanol and inhibits or decreases the generation of other acids and solvents. If acetone is to be manufactured as the predominate solvent, then the system would shift to mainly acetic acid in the major digestive pathway. We are breeding Clostridium acetobutylicium or other bacteria for their solventogenesis phase to increase cell mass proportionally to handle the increased volumetric productivity.

Thus, the invention uses the first bacteria to convert the carbohydrate feedstock to short chain organic acids and then uses the second bacteria to convert the short chain organic acids to short chain alcohols, also referred to as alkanols, and ketones. The term short chain refers to six or fewer carbon atoms in the chain, such as methanol, ethanol, propanol, butanol, pentanol and hexanol.

EXAMPLES

The following fermentations compare the separate microbial pathways using anaerobic and sterile conditions according to the invention with a single pathway. The results are set forth in Examples 1 & 2 and Tables 4 and 5 respectively. Both tables present data based on a comparison of the fermentations of a two bacterial process and a single microbe systems. Table 4 represents data in which the yield from the current invention is compared to the yield of the standard method for producing butanol (Weizmann, 1919). Table 5 represents data in which the volumetric productivity is compared to standard methods for producing butanol. The standard method for producing butanol uses a single microbe of Clostridium acetobutylicum via batch fermentation and was carried out according to the Weizmann process.

Microbes from American Type Culture Collection, Rockville, Md., are Clostridium acetobutylicum ATCC 4259, Clostridium thermobutyricum ATCC 49875, and Clostridium tyrobutyricum ATCC 25755.

Each reactor inherently incorporates cell recycling using a Carbosep M6 microfiltration membrane. Tangential flow and cross-membrane pressure brought to a steady state of 5 meters per second and a 0.75 bar respectively with a permeate flow rate of 2.5 liters per hour. This allows the cell concentration to remain in a steady state with the input from separate inoculation reactors supplying new cells which stabilizes growth rates.

Each reactor also inherently incorporates a liquid purification process which removes acids and solvents through activated charcoal and/or membrane technology and carbohydrates through sedimentation and/or centrifugation. This is done to remove digested carbohydrates and to remove acids or solvents for a given bacteria, either transferring for further conversion in the case of acids or for the purification as with solvents. This keeps the microbe functioning productively for the longer period of time.

By removing the acids as they are being produced in this invention fluctuations in pH and cell growth rate are stabilized. A balance for maximum solvent production is a function of carbohydrate feedrate, cell concentration, acid removal and transfer rates, temperature, and pH.

The optimum conditions of a given reactor is controlled for the specific reactor and the microbe used. This is done by controls and systems known to those in the art.

In preliminary laboratory experiments gas chromatography analytical procedures were employed to determine the quantities of acetone, ethanol, butanol, acetic acid, and butyric acid produced. A Varian model 3700 was used, employing a 5 foot×⅛ inch diameter stainless steel carbowax packed column. A Varian CDS-111 integrator was used for data analysis along with a Heath EU-208 chart recorder. N-propanol was used as the internal standard.

Carbohydrate concentration and dilution rates for continuous reactions are maximized for each microbe, controlling individual physiologies and production rates. The cell recycling dilution rate plus supply of fresh cells from individual inoculation reactor for each strain used, controls cell concentration.

The fermentation process conducted uses conventional procedures, with the exception that two or more bacteria are grown for their unique properties in accordance with the principles of this invention. The cultures are initially grown in serum bottles containing Thioglycollate medium before being transferred to inoculation reactors.

First the *C. acetobutylicum* system is brought up to a continuous steady state using two separate reactors. The acidogenesis reactor is kept at a pH of 5–7, temperature of 36° C. to promote the acidogenesis physiology of *C. acetobutylicum*. The rate of addition of carbohydrates into this minor path acidogenesis reactor must be such that they are completely displaced in a time within the normal logarithmic growth period of the organism employed without going into solventogenesis physiology. This stage is very productive and active in yielding acids and carbon dioxide. This secondary (minor) digestive path is brought to life in the beginning so as to generate continuous steady state *C. acetobutylicum's* solventogenesis physiology in order to convert the acids generated by the primary (major) digestive path into solvents. The cell mass from the acidogenic breeder reactor of *C. acetobutylicum* is transferred to the solventogenesis (solvents) reactor. This solventogenesis reactor is kept at a pH of 4.0–4.5, temperature of 36° C., and yields more hydrogen than the first stage of the minor digestive pathway. This solventogenesis reactor also digests some added raw carbohydrates and converts acids present (mostly butyric) into solvents. The size of the solventogenesis reactor is 5 to 10 times larger than the acidogenesis reactor for *C. acetobutylicum*. This is due to the solventogenesis metabolic rate of the microbe being slower and the fact that excess butyric acid is being added from the primary (major) digestive pathway which produces a preponderance of butyric acid for this function.

The primary (major) digestive pathway is carried out according to the characteristics of the microbes of choice in the two examples which are *C. thermobutyricum* and *C. tyrobutyricum*. This reactor's function is to produce acids which are purified by membrane separator or other techniques known to the art, and transferred to the solventogenesis reactor for conversion to solvents. This fermentation is very active and faster in converting carbohydrates into acids with rapid evolution of carbon dioxide. In this manner the invention takes advantage of the increased rate of conversion of carbohydrates to mainly butyric acid by using the optimum conditions of pH and temperature.

EXAMPLE 1

In this example *C. acetobutylicum* (ATCC 4259) is used in the acidogenesis and solventogenesis reactors via a continuous process. The detention time of the carbohydrates in the acidogenesis reactor is sufficiently short so as to prevent the organism from continuing its normal life cycle beyond the active state. *Clostridium thermobutyricum* (ATCC 49875) is used in the reactor of the major digestive path. The yields shown in Table 4 illustrate the advantage of using the embodiment of the invention to increase butanol production by at least 39% compared to a batch process. In a fed-batch operation of a membrane-assisted extractive butanol fermentation total solvent yield was increased only 23% due to the reduction of acid production and the reuse of cells compared to a batch process.

TABLE 4

|  | Butyrate % | Acetate % | Butanol % |
|---|---|---|---|
| Major digestion: continuous *C. thermobutyricum* | 41.6 | 3.3 |  |
| Minor digestion: continuous Acidogenesis *C. acetobutylicum* |  |  |  |
| Solventogenesis: continuous *C. acetobutylicum* |  |  | 34.9 |
| Batch *C. acetobutylicum* |  |  | 25.1 |

Significant improvements are found in comparison to a straight batch fermentation. The total carbohydrate uptake per run raises to ten times that of the value normally found in a batch fermentation. The total solvent yield increased by 39% due to the reduction of other products of fermentation normally associated with *C. acetobutylicum*.

EXAMPLE 2

The increase in volumetric productivity (grams/liter/hour, g/l/h) is determined by using *C. acetobutylicum* (ATCC 4259) in the minor digestive path to develop its solventogenesis phase and the major digestive path uses *C. tyrobutyricum* (ATCC 25755). The volumetric productivity shown in Table IV illustrates the advantage of using the embodiment of the invention to increase butanol production by at least 78% over the highest volumetric productivity reported by Afschar (1985). Therefore the rate of solvent productivity is almost doubled.

TABLE 5

|  | Butyrat g/l/h | Butanol g/l/h |
|---|---|---|
| Major digestion: continuous *C. tyrobutyricum* | 9.5 |  |
| Solventogenesis: continuous *C. acetobutylicum* |  | 8.0 |
| Continuous *C. acetobutylicum* |  | 4.5 |

The fermentation may be continued for long periods of time without interruption. Consequently, it is not the intention to limit this invention to the particular examples disclosed. On the contrary, the intention is to cover all modifications falling within the spirit and scope of the invention as expressed in the appended claims.

The main advantage of the invention is that it will produce butanol much faster than any previous inventions. It further prevents fluctuations in pH and takes advantage of the unique properties of each microbe. These advantages have a great effect on overall productivity and in the reduction in the total cost of manufacturing the products.

While certain preferred embodiments of the present invention have been disclosed in detail, it is to be understood that various modifications may be adopted without departing from the spirit of the invention or scope of the following claims.

I claim:

1. A continuous process for preparing solvents by digesting carbohydrates in an anaerobic fermentation of a carbohydrate slurry, the method comprising:
   (a) feeding a major portion of the carbohydrate slurry and a first acid-producing *clostridium* bacteria into an acid reactor and effecting the continuous fermentation of the carbohydrate with the first bacteria to form a solution including a short chain organic acid;
   (b) feeding a minor portion of the carbohydrate slurry and a second solvent-producing *clostridium* bacteria into a breeder reactor to breed the second bacteria in an acidogenesis phase;
   (c) extracting acid solution from the acid reactor and transferring the acid to a solventogenesis reactor;
   (d) extracting the second acidogenesis bacteria from the breeder reactor and transferring the second bacteria into the solventogenesis reactor and effecting the anaerobic fermentation of the extracted acid with the second bacteria to form a solution including a short chain alcohol; and
   (e) extracting the alcohol solution from the solventogenesis reactor at a rate sufficient to maintain the solventogenesis fermentation.

2. A process in accordance with claim 1 wherein the acid-producing bacteria comprises a first strain of Clostridium and the solvent producing bacteria comprises a second strain of Clostridium.

3. A process in accordance with claim 1 wherein the acid-producing bacteria is a Clostridium strain selected from the group consisting of *C. tyrobutyricum, C. thermobutyricum, C. butyricum, C. cadaveros, C. cellobioparum, C. cochlearium, C. pasteurianum, C. roseum, C. rubrum,* and *C. sporogenes*.

4. A process in accordance with claim 1 wherein the solvent-producing bacteria is a solventogenesis phase of a Clostridium strain selected from the group consisting of *C. acetobutylicum, C. beijerinkii, C. aurantibutyricum,* and *C. tetanomorphum*.

5. A process in accordance with claim 1 wherein the acid-producing bacteria is a thermophilic bacteria.

6. A process in accordance with claim 1 wherein the acid-producing bacteria is a bacteria selected from the group consisting of *clostridium tyrobutyricum* and *clostridium thermobutyricum*, the solvent-producing bacteria is *clostridium acetobutylicum*, the short chain organic acid is butyric acid and the short chain alcohol is butanol.

7. A process in accordance with claim 1 wherein the alcohol solution further comprises acetone and wherein the process further comprises extracting the acetone.

8. A continuous process for preparing solvents by digesting carbohydrates principally comprising polysaccharides in an anaerobic fermentation of a carbohydrate slurry, the method comprising:
   (a) feeding a major portion of the carbohydrate slurry and a first acid-producing *clostridium* bacteria into an acid reactor and effecting the continuous fermentation of the carbohydrate with the first bacteria to form a solution including butyric acid;
   (b) feeding a minor portion of the carbohydrate slurry and a second butanol-producing *clostridium* bacteria into a breeder reactor to breed the second bacteria in an acidogenesis phase;
   (c) extracting butyric acid solution from the acid reactor and transferring the acid to a solventogenesis reactor;
   (d) extracting the second acidogenesis bacteria from the breeder reactor and transferring the second bacteria into the solventogenesis reactor and effecting the anaerobic fermentation of the extracted acid with the second bacteria to form a solution comprising butanol; and
   (d) extracting the butanol solution from the solventogenesis reactor at a rate sufficient to maintain the solventogenesis fermentation.

9. A process in accordance with claim 8 wherein the acid-producing bacteria comprises a first strain of Clostridium and the solvent producing bacteria comprises a second strain of Clostridium.

10. A process in accordance with claim 8 wherein the acid-producing bacteria is a Clostridium strain selected from the group consisting of *C. tyrobutyricum, C. thermobutyricum, C. butyricum, C. cadaveros, C. cellobioparum, C. cochlearium, C. pasteurianum, C. roseum, C. rubrum,* and *C. sporogenes*.

11. A process in accordance with claim 10 wherein the butanol-producing bacteria is a Clostridium strain selected from the group consisting of *C. acetobutylicum, C. beijerinkii, C. aurantibutyricum,* and *C. tetanomorphum*.

12. A process in accordance with claim 8 wherein the acid-producing bacteria is a thermophilic bacteria.

* * * * *